US008435997B2

(12) United States Patent
Cook et al.

(10) Patent No.: US 8,435,997 B2
(45) Date of Patent: *May 7, 2013

(54) CYSTEINE PRODRUGS TO TREAT SCHIZOPHRENIA AND DRUG ADDICTION

(75) Inventors: James M. Cook, Milwaukee, WI (US); Edward Merle Johnson, II, Glendale, WI (US); David A. Baker, Grafton, WI (US); Wenyuan Yin, Milwaukee, WI (US)

(73) Assignees: Marquette University, Milwaukee, WI (US); UWM Research Foundation, Inc., Milwaukee, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/897,353

(22) Filed: Oct. 4, 2010

(65) Prior Publication Data

US 2011/0021533 A1    Jan. 27, 2011

Related U.S. Application Data

(62) Division of application No. 12/189,516, filed on Aug. 11, 2008, now Pat. No. 7,829,709.

(60) Provisional application No. 60/955,269, filed on Aug. 10, 2007.

(51) Int. Cl.
*A61K 31/497* (2006.01)
(52) U.S. Cl.
USPC ...................... 514/252.1; 544/405
(58) Field of Classification Search ............... 514/252.1; 544/408
See application file for complete search history.

(56) References Cited

U.S. PATENT DOCUMENTS

| 5,589,473 A | 12/1996 | Geiwiz et al. |
| 2005/0032708 A1 | 2/2005 | Bush et al. |
| 2006/0270647 A1 | 11/2006 | Coric et al. |

FOREIGN PATENT DOCUMENTS

| DE | 4228455 A1 | 9/1994 |
| EP | 0463514 A1 | 1/1992 |
| EP | 0499882 A1 | 8/1992 |
| EP | 0999204 A1 | 5/2000 |
| EP | 1004302 A2 | 5/2000 |
| EP | 1120407 A1 | 8/2001 |
| EP | 1195259 A2 | 4/2002 |
| EP | 1364943 A1 | 11/2003 |
| EP | 1374831 A1 | 1/2004 |
| FR | 2159183 A | 6/1973 |
| WO | 9118594 A1 | 12/1991 |
| WO | 9746229 A1 | 12/1997 |
| WO | 0137788 A1 | 5/2001 |
| WO | 2004030522 A2 | 4/2002 |
| WO | 02011676 A2 | 12/2002 |
| WO | 03045359 A2 | 6/2003 |
| WO | 2004108692 A1 | 12/2004 |
| WO | 2008008380 A1 | 1/2008 |

OTHER PUBLICATIONS

Bernstein, et al. Tetrahedron Letters, 26(16), 1985, 1951-1954.*
Angehrn, P. et al., "New Antibacterial Agents Derived from the DNA Gyrase Inhibitor Cyclothialidine," Journal of Medicinal Chemistry, American Chemical Society, Washington, US, vol. 47, No. 6, Jan. 1, 2004, pp. 1487-1513.
Braga, A. L. et al., "'One-Pot' Synthesis of Chiral N-Protected alpha-Amino Acid-Derived 1,2,4-Oxadiazoles," Synthesis, May 26, 2004, pp. 1589-1594.
Grzonka, Z. et al., "Chiroptical Properties of Tetrazole Analogs of Amino Acids," Polish Journal of Chemistry, vol. 52, 1978, pp. 1411-1413.
Brook, et al. "Tetrazole analogues of amino acids and peptides: II. Paper and thin-layer chromatography of tetrazole analogues of amino acids," Journal of Chomatography, vol. 15, No. 2, 1970, pp. 310-313.
Shumpei Sakaibara, Hisaya Tani: "Synthesis of Polycysteine," Bull. Chem. Soc., Japan, vol. 29, 1956, pp. 85-88.
Erwin Brand, Marta Sandberg: "The lability of the sulfur in cystine derivatives and its possible bearing on the constitution of insulin," J. Biol. Chem., vol. 70, 1926, pp. 381-395.
Database Crossfire Beilstein Beilstein Institute Zur Foerderung Der Wissenschaften, Franfurt Am Main, DE; Database accession No. 5753808 & Marc J. O. Anteunis, Chr. Becu, A. Kolodziejcz;yk, Bogdan Liberek: Bull. Soc. Chim. Belges, vol. 90, No. 8, 1981, pp. 785-802.
Database Crossfire Beilstein Beilstein Institute Zur Foerderung Der Wissenschaften, Franfurt Am Main, DE; Database accession No. 5753809 & A. Kolodziejczyk, Bogdan Liberek: Bull. Soc. Chim. Belges, vol. 90, No. 8, 1981, pp. 785-802.
Database Crossfire Beilstein Beilstein Institute Zur Foerderung Der Wissenschaften, Franfurt Am Main, DE; Database accession No. 844285 & Blaha et al.: Collection of Czechoslovak Chemical Communications, vol. 31, 1966, pp. 4296-4298.
Database Crossfire Beilstein Beilstein Institute Zur Foerderung Der Wissenschaften, Franfurt Am Main, DE; Database accession No. 3978029 & Blaha et al.: Collection of Czechoslovak Chemical Communications, vol. 31, 1966, pp. 4296-4298.
Database Crossfire Beilstein Beilstein Institute Zur Foerderung Der Wissenschaften, Franfurt Am Main, DE; Database accession No. 72669 & Jesse P. Greenstein: "Studies of multivalent amino acids and peptides" J. Biol. Chem., vol. 118, No. 2, 1937, pp. 321-329.
Database Crossfire Beilstein Beilstein Institute Zur Foerderung Der Wissenschaften, Franfurt Am Main, DE; Database accession No. 800081 & A. P. Hope, B. Halpern: Australian Journal of Chemistry, vol. 29, 1976, pp. 1591-1603.
Database Crossfire Beilstein Beilstein Institute Zur Foerderung Der Wissenschaften, Franfurt Am Main, DE; Database accession No. 665766 & Wenck, Schneider: Experientia, vol. 27, 1971, pp. 20-22.
Database Crossfire Beilstein Beilstein Institute Zur Foerderung Der Wissenschaften, Franfurt Am Main, DE; Database accession No. 60079 & Abderhalden, Rossner: Hoppe-Seyler's Zeitschrift Fur Physiologische Chemie, vol. 163, 1927, p. 183.
G. Zanotti, F. Pinnen, G. Lucente: Tetrahedron Letters, vol. 26, No. 44, 1984, pp. 5481-5484.

(Continued)

*Primary Examiner* — Douglas M Willis
(74) *Attorney, Agent, or Firm* — Quarles & Brady LLP

(57) ABSTRACT

The present invention provides cysteine prodrugs for the treatment of schizophrenia and drug addiction. The invention further encompasses pharmaceutical compositions containing prodrugs and methods of using the prodrugs and compositions for treatment of schizophrenia and drug addiction.

10 Claims, 9 Drawing Sheets

OTHER PUBLICATIONS

Karl-Hans Ongania: "Selektive Eliminations-Additionsreaktionen" Arch. Pharm., vol. 312, 1979, pp. 963-968.

Database Crossfire Beilstein Beilstein Institute Zur Foerderung Der Wissenschaften, Franfurt Am Main, DE; Database accession No. 50666 & Hooper et al.: J. Chem Soc., vol. 1956, 1956, pp. 3148-3151.

Hans Heymann, T. Ginsberg, Z. R. Gulick, E. A. Konopka, R. L. Mayer: "The preparation and some biological properties of the asparagine analog L-2-amino-2-carbocyethanesul fonamide" J. Am. Chem. Soc. vol. 81, 1959, pp. 5125-5128.

Database Crossfire Beilstein Beilstein Institute Zur Foerderung Der Wissenschaften, Franfurt Am Main, DE; Database accession No. 2635366 & Michael Ruf et al.: Chemische Berichte, vol. 129, No. 10, 1996, pp. 1251-1258.

Database Crossfire Beilstein Beilstein Institute Zur Foerderung Der Wissenschaften, Franfurt Am Main, DE; Database accession No. 6702116 & L. Servas, I. Photaki: J. Am. Chem. Soc., vol. 84, 1962, pp. 3887-3897.

Database Crossfire Beilstein Beilstein Institute Zur Foerderung Der Wissenschaften, Franfurt Am Main, DE; Database accession No. 2635070 & Fry: J. Org. Chem., vol. 15, 1950, pp. 438-441.

Database Crossfire Beilstein Beilstein Institute Zur Foerderung Der Wissenschaften, Franfurt Am Main, DE; Database accession No. 3187303 & Foeldi: Acto Chimica Academiae Scientarum Hungaricae, vol. 5, 1955, pp. 187-194.

Database Crossfire Beilstein Beilstein Institute Zur Foerderung Der Wissenschaften, Franfurt Am Main, DE; Database accession No. 2611160 & L. Servas, I. Photaki: J. Am. Chem. Soc., vol. 84, 1962, pp. 3887-3897.

Database Crossfire Beilstein Beilstein Institute Zur Foerderung Der Wissenschaften, Franfurt Am Main, DE; Database accession No. 1730085 & Pirie: Biochemical Journal, vol. 25, 1931, p. 619.

Database Crossfire Beilstein Beilstein Institute Zur Foerderung Der Wissenschaften, Franfurt Am Main, DE; Database accession No. 10718042 & Eiji Kawanishi, Kyoichi Higuchi, Akihiko Ishida: Heterocycles, vol. 52, No. 1, 2000, pp. 425-443.

Database Crossfire Beilstein Beilstein Institute Zur Foerderung Der Wissenschaften, Franfurt Am Main, DE; Database accession No. 10724708 & Eiji Kawanishi, Kyoichi Higuchi, Akihiko Ishida: Heterocycles, vol. 52, No. 1, 2000, pp. 425-443.

Database Crossfire Beilstein Beilstein Institute Zur Foerderung Der Wissenschaften, Franfurt Am Main, DE; Database accession No. 3986193 & Blaha et al.: Collection of Czechoslovak Chemical Communications, vol. 31, 1966, pp. 4296-4298.

Database Crossfire Beilstein Beilstein Institute Zur Foerderung Der Wissenschaften, Franfurt Am Main, DE; Database accession No. 5323681 & A. I. Meyers, Richard A. Amos: J. Am. Chem. Soc., vol. 102, No. 2, 1980, pp. 870-872.

Database Crossfire Beilstein Beilstein Institute Zur Foerderung Der Wissenschaften, Franfurt Am Main, DE; Database accession No. 2200873 & T. Inui: Bull. Soc. Chem. Japan, vol. 44, No. 9, 1971, pp. 2515-2520.

Baker et al. Neuroadaptations in cystine-glutamate exchange underlie cocaine relapse. Nat Neurosci 2003; 6: 743-749.

Baker et al. Contribution of cystine-glutamate antiporters to the psychotomimetic effects of phencyclindine. Neuropsychopharmacology 2008; 33: 1760-1772.

Berk M. Oxidative stress in bipolar disorder: a double blind randomized placebo controlled trial of N-actyl cysteine as glutathione precursor. Bipolar Disorders 2007; 9(suppl 1): 21.

Larowe et al. Safety and tolerability of N-acetylcysteine in cocaine-dependent individuals. Am J Addict 2006; 15: 105-110.

Madayag et al. Repeated N-acetylcysteine administration alters plasticity-dependent effects of cocaine. J Neurosci 2007; 27: 13968-13976.

Mardikian et al. An open-label trial of N-acetylcysteine for the treatment of cocaine depedence: a pilot study. Prog Neuropsychopharmacol Biol Psychiatry 2007; 31: 389-394.

Moran et al. Cystine/glutamate exchange regulates metabotropic glutamate receptor presynaptic inhibition of excitatory transmission and vulnerability to cocaine seeking. J Neurosci 2005; 25: 6389-6393.

Peters et al. The group II metabotropic glutamate receptor agonist, LY379268, inhibits both cocaine- and food-seeking behavior in rats. Psychopharmacology 2006; 186: 143-149.

Zhao et al. The enantiospecific, stereospecific total synthesis of the ring-A oxygenated sarpagine indole alkaloids (+)-Majvininve, (+)-10-Methoxyaffinisine, and (+)-Na-Methylsarpagine, as well as the total synthesis of the alstonia bisindole alkaloid macralstonidine. J. Org. Chem. 2003; 68: 6279-6295.

Sheehan et al. A new synthesis of cysteinyl peptides. J. Am. Chem. Soc. 1958; 80:1158-1164.

Bressan et al. Synthesis and metal-coordination properties of dimeric cyclo-L-hemicystinyl-glycine. Int. J. Peptide Protein Res. 1986; 28:103-106.

Bernstein et al. Preparation of a diketopiperazine analog of leukotriene D4 (LTD4). Tetrahedron Lett. 1985; 26:1951-1954.

Bull et al. Practical synthesis of schollkopf's bis-lactim ether chiral auxiliary: (3S)-3,6-dihydro-2,5-dimethoxy-3-isopropyl-pyrazine. Tetrahedron:Asymmetry 1998; 9:321-327.

Berk et al. N-acetyl cysteine as a glutathione precursor for schizophrenia—a double-blind, randomized, placebo-controlled trial. Biol. Psychiatry 2008; 64:468-475.

Abderhalden et al. Weitere Beiträge über Dioxo-piperazine sowie über ein aus Leucyl-glycinanhydrid gewonnenes, ungesättiges Anhydrid. Synthese des tertiären Leucins. Z Physiol Chem 1927; 163:149-184.

Rossbach et al. Synthese and Eigenschaften unsymmetrischer Diketopiperazine des Cysteins. Z Naturforsch B 1971; 26:1144-1151.

Bergmann et al. Umlagerungen peptidähnlicher Stoffe. 7. Unwandlung eines cystinhaltigen Diketopiperazines. Z Physiol Chem 1926; 152:189-201.

Schneider et al. Kinetics of the reaction of imidazolesulfhydryl compounds with N-ethylmaleimide. Hoppe-Seyler's Z. Physiol. Chem., 1969; 350:1521-1530.

Gockel et al. Zinc complexation of cyclic dipeptides containing cysteine and/or histidine. Inorg. Chim. Acta., 2001; 323:16-22.

Greenstein et al. Multivalent amino acids and peptides. VIII. Synthesis of bisanhydro-l-cystinyl-l-cystine and other diketopiperazines of cystine. J. Biol. Chem., 1937; 118:321-329.

Schneider F. Kooperative Imidazol-SH-Katalyse als enzymatische Modellreaktion. Hoppe-Seyler's Z. Physiol. Chem., 1967; 348:1034-1042.

Fischer et al. A diketopiperazine derivative with antibacterial activity. Rev. Asoc. Med. Argent., 1955, 69:21-22.

* cited by examiner

CYSTEINE PRODRUGS TO TREAT SCHIZOPHRENIA AND DRUG ADDICTION

CROSS-REFERENCE TO RELATED APPLICATIONS

This application is a divisional of U.S. application Ser. No. 12/189,516, filed on Aug. 11, 2008, which claims the benefit of U.S. Application No. 60/955,269, filed Aug. 10, 2007. Both applications are incorporated by reference herein in their entirety.

FIELD OF THE INVENTION

This invention relates generally to the treatment of schizophrenia and drug addiction. More particularly, the present invention is directed to cysteine prodrugs useful as antipsychotic medications in the treatment of schizophrenia. As well, the respective prodrugs are applicable for reducing drug cravings in drug addicted individuals.

BACKGROUND OF THE INVENTION

Schizophrenia is a debilitating disorder afflicting 1% of the world's population. The development of effective medications to treat schizophrenia is reliant on advances in characterizing the underlying pathophysiology. Chlorpromazine and other phenothiazines are considered first generation antipsychotics (termed "typical antipsychotics") useful in the treatment of schizophrenia. However, the antipsychotic efficacy of phenothiazines was, in fact, serendipitously discovered. These drugs were initially used for their antihistaminergic properties and later for their potential anesthetic effects during surgery. Hamon and colleagues extended the use of phenothiazines to psychiatric patients and quickly uncovered the antipsychotic properties of these compounds; shortly thereafter, the pharmacologic characteristic of dopamine receptor blockade was linked to the antipsychotic action of chlorpromazine (Thorazine). This led to the development of additional dopamine receptor antagonists, including haloperidol (Haldol). For nearly fifty years, dopamine antagonists were the standard treatment for schizophrenia even though these drugs induce severe side effects ranging from Parkinson's disease-like motor impairments to sexual dysfunction and are only effective in treating the positive symptoms of schizophrenia.

In the 1970's, clozapine became the first "atypical psychotic" or 2nd generation antipsychotic agent introduced. Clinical trials have shown that clozapine produces fewer motor side effects and exhibits improved efficacy against positive and negative symptoms relative to 1st generation compounds. However, clozapine was briefly withdrawn from the market because of the potential to produce severe agranulocytosis, a potentially fatal side effect requiring patients to undergo routine, costly hematological monitoring. As a result, clozapine is only approved for treatment-resistant schizophrenia. Although also a dopamine receptor antagonist, the therapeutic site of action for clozapine is thought to involve, at least in part, blockade of serotonin receptors. This led to the generation of other serotonin receptor antagonists in the 1990's with the goal of improving the safety profile of clozapine.

The growth potential for novel antipsychotics was revealed following the introduction of risperidone in 1994; within two years risperidone overtook haloperidol in the number of prescriptions written by physicians. While it was generally assumed that the newer 2nd generation antipsychotics also exhibited the favorable efficacy profile produced by clozapine, the clinical data was ambiguous. As a result, the NIH recently funded a large, lengthy, and expensive clinical trial to examine this assumption. The results of the Clinical Antipsychotic Trials of Intervention Effectiveness (CATIE), recently released, indicate that there is no benefit to the newer 2nd generation compounds. Specifically, 1st and 2nd generation drugs did not differ in the incidence of severe motor side-effects nor were 2nd generation agents found to be more effective than 1st generation antipsychotics. In the CATIE trial, 74% of the patients discontinued treatment prior to completing the 18 month trial, in part due to a lack of efficacy and intolerability of the treatment regimen.

Uncontrolled drug use and heightened susceptibility to relapse are defining features of addiction that contribute to the transition in drug consumption from a recreational to a compulsive pattern. Long-term plasticity resulting in augmented excitatory neurotransmission within corticostriatal pathways in response to drugs of abuse have been implicated in addiction. Human cocaine abusers exposed to craving-inducing stimuli exhibit increased activation of excitatory circuits originating in cortical regions, including orbital and prefrontal cortex, and projecting to the ventral striatum; further, the degree of activation of corticostriatal pathways correlates with craving in humans. Preclinical data also indicate the existence of drug-induced plasticity leading to increased activation of corticostriatal pathways following exposure to drugs or drug-paired cues. Activation of these circuits results in heightened extracellular glutamate in the nucleus accumbens and stimulation of ionotropic glutamate receptors, both of which are necessary for cocaine primed reinstatement. Further, the dorsomedial prefrontal cortex has been shown to be necessary for reinstatement produced by exposure to drug-paired cues using the contextual reinstatement paradigm and in response to electrical foot shock. As a result, identification of cellular mechanisms capable of regulating synaptic glutamate represent targets in the treatment of addiction.

As can be appreciated from the foregoing, there exists a pressing need and considerable market potential for novel antipsychotic and anti-drug craving agents. Of course, the development of such agents will be facilitated by a thorough understanding of pathophysiologies underlying the neurological disorders.

SUMMARY OF THE INVENTION

The present invention is based on the inventors' success in identifying derivatives of cysteine with demonstrated utility as antipsychotic and anticraving agents. Accordingly, the present invention provides cysteine prodrugs having the structure:

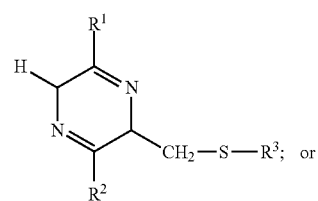

a cystine dimer of the prodrug having the structure:

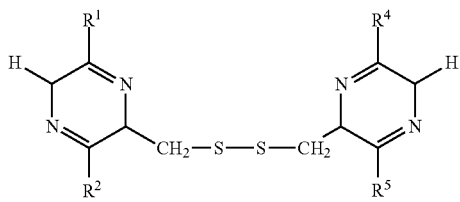

wherein: $R^1$, $R^2$, $R^4$ and $R^5$ are independently selected from OH, =O, or a branched or straight chain $C_1$ to $C_5$ alkoxyl group, with the caveats that when =O is selected the nitrogen atom adjacent the carbonyl group thusly formed bears a H and a single bond joins the adjacent nitrogen to the carbonyl group and further $R^1$, $R^2$, $R^4$ and $R^5$ shall be selected to not all be =O; and $R^3$ is H, a branched or straight chain $C_1$ to $C_5$ alkyl, a nitrobenzenesulfonyl, an aryl thio, an aryl, an alkylthio, an acyl, a benzoyl, a thio acyl, a thio benzoyl, or a benzyl group.

Certain preferred prodrugs according to the invention have formulas in which $R^1$, $R^2$, $R^4$ and $R^5$ are independently selected from the branched or straight chain $C_1$ to $C_5$ alkoxyl group. Yet other preferred prodrugs according to the invention have formulas in which $R^1$, $R^2$, $R^4$ and $R^5$ are selected from the same branched or straight chain $C_1$ to $C_5$ alkoxyl group. One particularly preferred cysteine prodrug according to the invention has the structure:

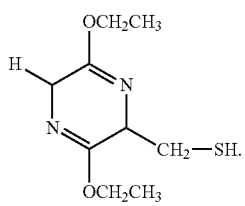 [SMILES: CCOC1=NC(CS)C(OCC)=NC1]

Cysteine prodrugs according to the invention are further provided in the form of cystine dimers, a particularly preferred dimer having the structure:

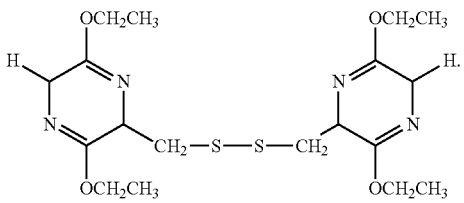

In certain embodiments, the invention encompasses pharmaceutical compositions comprising a cysteine prodrug or dimer thereof as described and claimed herein in combination with a pharmaceutically-acceptable carrier.

In another aspect, the invention is directed to a method of reducing schizophrenia in a subject. Such a method includes steps of administering to the subject an effective amount of a cysteine prodrug or dimer thereof, whereby schizophrenia is reduced in the subject. Administration of the cysteine prodrug or dimer is preferably accomplished by oral delivery.

In yet another aspect, the invention encompasses a method of reducing drug craving in a subject. Such a method includes steps of administering to the subject an effective amount of a prodrug or dimer, whereby drug craving is reduced in the subject.

Preferred prodrugs for use in treatment methods according to the invention include the prodrug having the structure:

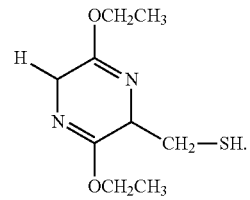 [SMILES: CCOC1=NC(CS)C(OCC)=NC1]

A preferred prodrug in dimer form for use in the inventive methods is the cystine dimer having the structure:

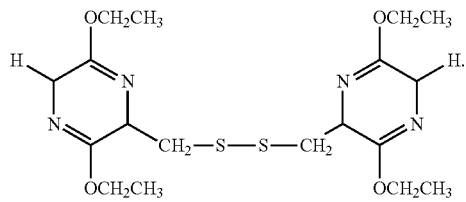

The invention also provides a method of reducing schizophrenia in a subject comprising administering to the subject an effective amount of a cysteine prodrug having the structure:

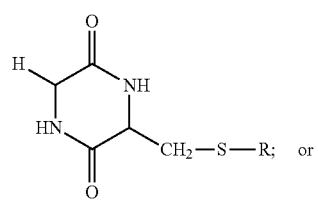

a cystine dimer of the prodrug having the structure:

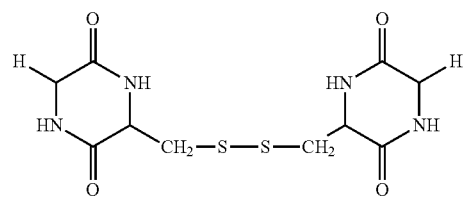

wherein R is H, a branched or straight chain $C_1$ to $C_5$ alkyl, a nitrobenzenesulfonyl, an aryl thio, an aryl, an alkylthio, an acyl, a benzoyl, a thio acyl, a thio benzoyl, or a benzyl group, whereby schizophrenia is reduced in the subject. The preferred route of administration is by oral delivery.

In certain methods of reducing schizophrenia, the cysteine prodrug administered to the subject has the structure:

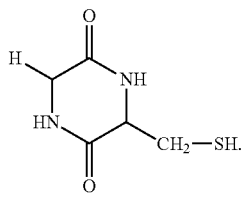

In another aspect, the invention is directed to a method of reducing drug craving in a subject comprising administering to the subject an effective amount of a cysteine prodrug having the structure:

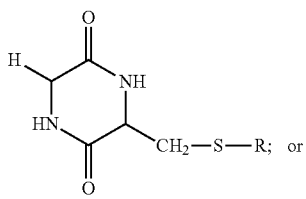

a cystine dimer of the prodrug having the structure:

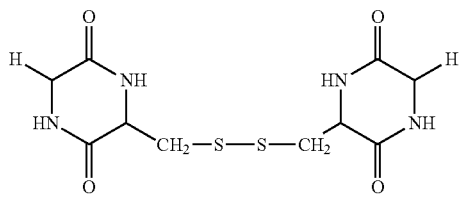

wherein R is H, a branched or straight chain $C_1$ to $C_5$ alkyl, a nitrobenzenesulfonyl, an aryl thio, an aryl, an alkylthio, an acyl, a benzoyl, a thio acyl, a thio benzoyl, or a benzyl group, whereby drug craving is reduced in the subject. The preferred route of administration is by oral delivery.

In certain methods of reducing drug craving, the cysteine prodrug administered to the subject has the structure:

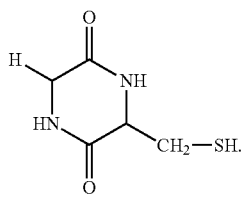

Other objects, features and advantages of the present invention will become apparent after review of the specification, claims and drawings.

DETAILED DESCRIPTION OF THE INVENTION

Figure 1:
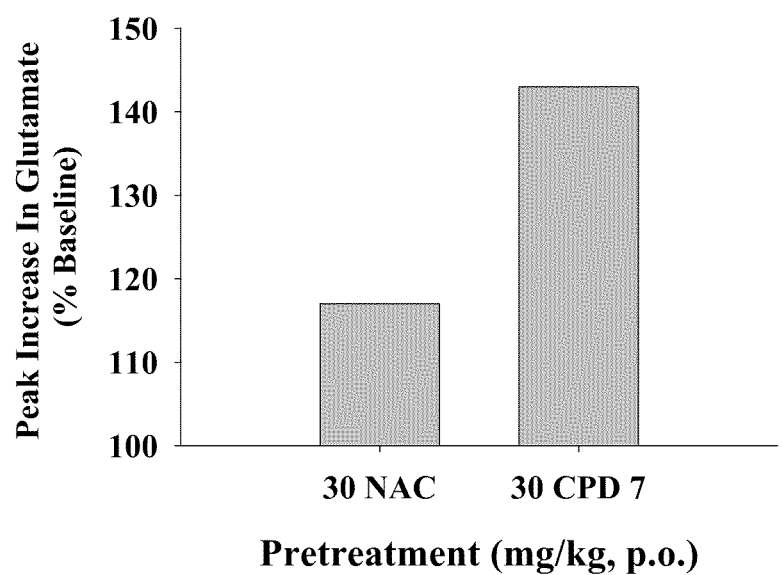
FIG. 1 depicts a bar graph indicating an increase in extracellular glutamate in the prefrontal cortex (relative to baseline) is greater following administration of compound 7 shown in Scheme 1 (30 mg/kg, po; N=1); than cysteine prodrug N-acetylcysteine (60 mg/kg, IP; N=4).

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

In the embodiments described herein and unless indicated otherwise, the term "alkyl" shall mean a straight or branched, substituted or unsubstituted alkyl group having 1-5 carbon atoms. By "cycloalkyl" it is meant a ring compound containing 3-7 carbon atoms. Also, the term "aromatic" refers to cyclic or heterocyclic compounds displaying aromaticity. As used herein, the term "alkoxyl" group refers to an alkyl (as defined above) group linked to oxygen to provide the general chemical moiety —OR.

As used herein, the term "administering" refers to bringing a subject, tissue, organ or cells in contact with the cysteine prodrugs described in this disclosure. In certain embodiments, the present invention encompasses administering the compounds useful in the present invention to a patient or subject. A "subject", "patient" and "individual", used equivalently herein, refers to a mammal, preferably a human, that either: (1) has a disorder remediable, treatable, or diminished in severity by administration of cysteine prodrugs and dimers thereof according to the invention; or (2) is susceptible to a disorder that is preventable by administering same.

As used herein, the terms "effective amount" and "therapeutically effective amount" refer to the quantity of active therapeutic agents sufficient to yield a desired therapeutic response without undue adverse side effects such as toxicity, irritation, or allergic response. The specific "effective amount" will, obviously, vary with such factors as the particular condition being treated, the physical condition of the patient, the duration of the treatment, the nature of concurrent therapy (if any), and the specific formulations employed. In this case, an amount would be deemed therapeutically effective if it resulted in one or more of the following: (a) the prevention of schizophrenia and/or drug craving; and (b) the reduction or stabilization of schizophrenia and/or drug craving. The optimum effective amounts can be readily determined by one of ordinary skill in the art using routine experimentation.

The present inventors have recently identified the cystine-glutamate antiporter as a highly novel cellular process that likely contributes to the pathology underlying schizophrenia and drug addiction. Importantly, the inventors have collected the first data set indicating that cysteine prodrugs, used to increase the activity of cystine-glutamate antiporters, block cognitive deficits and social withdrawal in the preclinical phencyclidine model of schizophrenia. Unlike existing medications, cysteine prodrugs appear to exert antipsychotic properties, in part, by reversing pathology underlying the disease.

While no one theory or mechanism of pharmacological effect is adopted herein, cysteine prodrugs appear to restore diminished signaling to glutamate receptors and diminished glutathione levels observed in schizophrenics. A depleted glutathione level can lead to increased oxidative stress, and impaired cystine-glutamate antiporter activity, glutamate neurotransmission, synaptic connection, and gene expression, all of which are observed in schizophrenia.

Increased excitatory neurotransmission in the nucleus accumbens may arise, in part, by diminished activity of cystine-glutamate antiporters. The recent data collected by the present inventors illustrates that glutamate released from these antiporters provides endogenous tonic stimulation to group II or 2/3 metabotropic glutamate receptors (mGluRas) and thereby regulates synaptic glutamate and dopamine release. Thus, altered glutamate signaling could arise as a consequence of decreased cystine-glutamate exchange. Repeated cocaine administration has been shown to blunt the activity of cystine-glutamate exchange, which likely contributes to a sequence of events, including diminished group II mGluR autoregulation and increased excitatory neurotransmission in the nucleus accumbens.

Impaired cystine-glutamate antiporter activity and faulty glutamate neurotransmission bear on the issue of uncontrolled drug use, i.e., drug addiction. Cysteine prodrugs, such as N-acetylcysteine ("NAC"), are used to drive cystine-glutamate exchange by apparently elevating extracellular cystine levels, thereby creating a steep cystine concentration gradient. Preclinical studies have shown N-acetylcysteine to be effective in blocking compulsive drug-seeking in rodents. Further, extant clinical data also show a reduction in cocaine use and craving in cocaine abusers receiving NAC. Unfortunately, the full clinical efficacy of targeting cystine-glutamate exchange may be unrealized when utilizing NAC due to extensive first-pass metabolism and limited passive transport of this drug across the blood-brain barrier. The prodrugs described and claimed herein are not significantly eliminated by the liver and will readily pass the blood-brain barrier. Cysteine is the reduced form of cystine and is readily oxidized in vivo to cystine, thus elevating either cysteine or cystine is believed to increase cystine-glutamate exchange.

The cysteine prodrug NAC has been previously shown to have a favorable safety/tolerability profile in human subjects. In fact, NAC has been used for decades in humans for other indications (e.g., as a mucolytic, acetaminophen toxicity) and as an experimental treatment (HIV, cancer) without producing severe adverse effects. However, NAC undergoes extensive first pass metabolism requiring the usage of high doses that limit the utility of the drug and, potentially, increase the chances of side effects due to the buildup of metabolized by-products. The prodrugs presently disclosed and claimed herein are designed to substantially avoid the problem of first pass metabolism and poor blood brain barrier permeability, and therefore exhibit increased efficacy as compared to prior cysteine prodrugs as illustrated by improved potency and/or efficacy.

Repeated cocaine alters glutamate neurotransmission even following protracted withdrawal, and this likely contributes to addiction since abnormal activation of corticostriatal pathways correlates with craving in humans and is necessary for cocaine seeking in rodents. Revealing cellular mechanisms underlying altered corticostriatal activation should advance our understanding of the neurobiological basis of addiction and identify novel therapeutic targets.

Models of pathological glutamate signaling proposed to underlie addiction need to account for the existence of multiple pools of extracellular glutamate. Aside from synaptic glutamate maintained by vesicular release, extrasynaptic glutamate is sustained primarily by nonvesicular release. In support, basal extrasynaptic glutamate sampled using microdialysis are largely independent of vesicular glutamate. Glutamate transporters may partition the two pools by limiting glutamate overflow from the synapse into extrasynaptic compartments, and restricting entry of nonvesicular glutamate into synapses. Although confined to the extrasynaptic compartment, nonvesicular glutamate regulates neurotransmission by stimulating group II metabotropic glutamate receptors (mGluRs) which are extrasynaptic receptors capable of inhibiting vesicular release. Thus, extrasynaptic receptors permit crosstalk between the two pools and indicate that altered nonvesicular glutamate release may contribute to pathological glutamate signaling linked to addiction.

Cystine-glutamate exchange via the cystine/glutamate transporter system may be critical in the capacity of extrasynaptic glutamate to regulate corticostriatal signaling in the normal and pathological states. First, nonvesicular release from cystine-glutamate exchange maintains basal extracellular glutamate in the nucleus accumbens, and thereby regulates the extent of endogenous group II mGluR stimulation. Repeated cocaine blunts transporter activity which leads to reduced basal and increased cocaine-evoked glutamate in the nucleus accumbens that persists for at least three weeks after the last cocaine treatment. These changes are relevant for drug seeking since N-acetylcysteine, a cysteine prodrug used to drive the transporter system, blocks cocaine-evoked glutamate in the nucleus accumbens and subsequent cocaine-induced reinstatement.

Depicted below in Scheme 1 is the general synthetic route for manufacturing cysteine prodrugs and dimers according to the invention, including specific prodrugs 4 and 5 which are exemplary chemical entities useful in the invention. Exemplary cystine dimers joined by disulfide linkages and corresponding to prodrugs 4 and 5 are illustrated as compounds 7 and 6, respectively. The chemistry employed in the manufacture of prodrugs according to the invention is adapted, in part, on Scholkopf chiral auxiliary chemistry described in the literature (indicated by a superscript [c] throughout Scheme 1; see, e.g., Zhao, S. et al.). Example 1 of this disclosure provides additional detailed description of the chemical syntheses of Scheme 1.

Further referring to Scheme 1, compounds 8a and 8b represent partially alkylated derivatives of respective compound 5, effectively intermediates between compound 5 and compound 4 as compound 5 undergoes metabolism to yield compound 4 following administration of compound 5 to a subject. Likewise, compounds 9a and 9b represent partially alkylated derivatives of respective compound 6, effectively intermediates between compound 6 and compound 7 following administration of compound 6 to a subject. As can be appreciated, compounds 8a, 8b, 9a, 9b and similar partially alkylated versions of compounds according to the invention can themselves serve as cysteine prodrugs and may therefore be administered by the methods described and claimed herein.

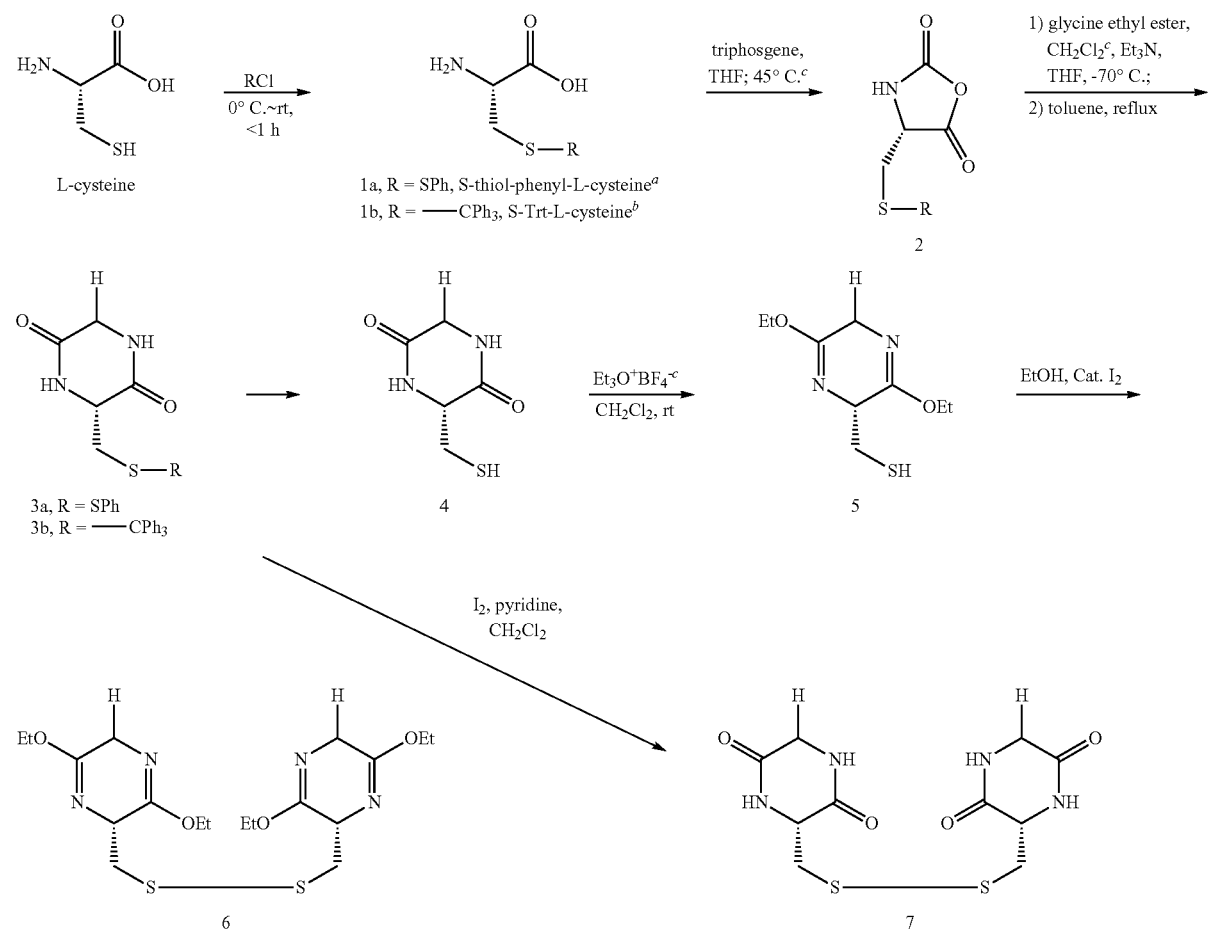

-continued a) Sakakibara, S.; Tani, H. Synthesis OF Polycysteine. Bull Chem. Soc. (Japan), 29, 85-88 (1956).
b) Zervas, L.; Photaki, I. On Cysteine and Cystine Peptides. I. New S-Protecting Groups for Cysteine. J. Am. Chem. Soc., 84, 3887-3897 (1962).
c) Zhao, S.; Liao, X.; Wang, T.; Flippen-Anderson, J.; Cook, J.M.; The Enantiospecific, Stereospecific Total Synthesis of the Ring-A Oxygenated Sarpagine Indole Alkaloids (+)-Majvinine, (+)-10-Methoxyaffinisine, and (+)-N$_a$-Methylsarpagine, and Well as the Total Synthesis of the Alstonia Bisindole Alkaloid Macralstonidine. J. Org. Chem., 68, 6279-6295 (2003).

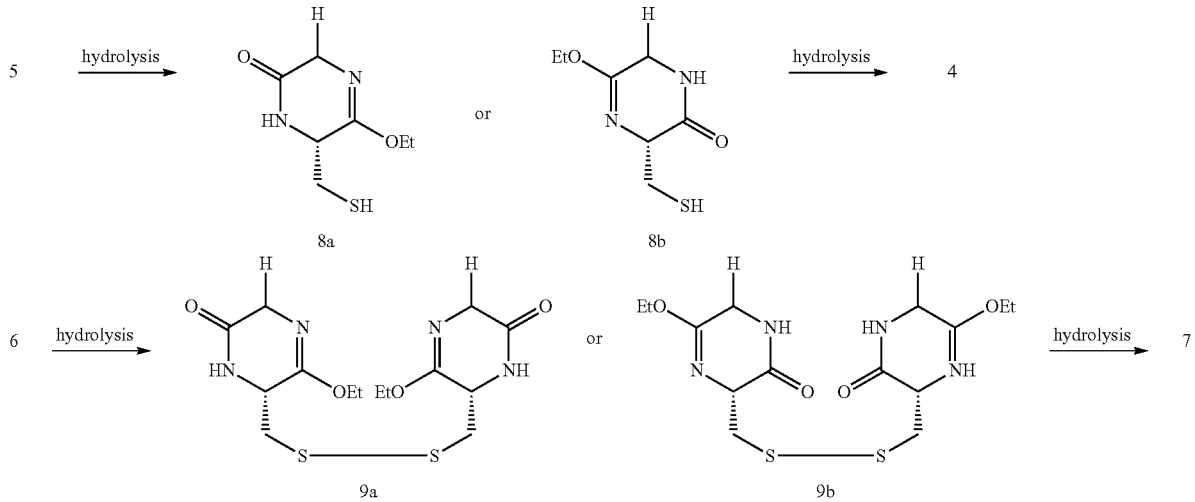

Upon administration to a subject, prodrugs and dimers according to the invention pass largely intact through first pass metabolism other than the hydrolysis reactions shown in Scheme 1. Such prodrugs and dimers are eventually cleaved into the corresponding amino acids by peptidases in cells contained within the central nervous system (CNS).

Accordingly, the present invention is directed to cysteine prodrugs having the structure:

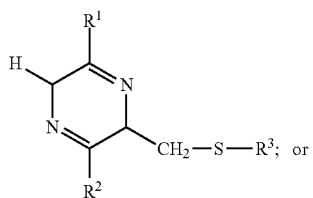

a cystine dimer of the prodrug having the structure:

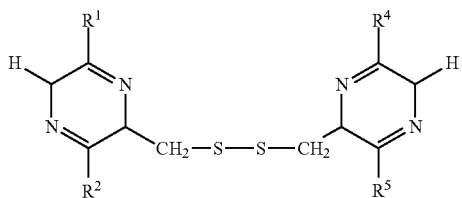

wherein: $R^1$, $R^2$, $R^4$ and $R^5$ are independently selected from OH, =O, or a branched or straight chain $C_1$ to $C_5$ alkoxyl group, with the caveats that when =O is selected the nitrogen atom adjacent the carbonyl group thusly formed bears a H and a single bond joins the adjacent nitrogen to the carbonyl group and further $R^1$, $R^2$, $R^4$ and $R^5$ shall be selected to not all be =O; and $R^3$ is H, a branched or straight chain $C_1$ to $C_5$ alkyl, a nitrobenzenesulfonyl, an aryl thio, an aryl, an alkylthio, an acyl, a benzoyl, a thio acyl, a thio benzoyl, or a benzyl group.

Certain preferred prodrugs according to the invention have formulas in which $R^1$, $R^2$, $R^4$ and $R^5$ are independently selected from the branched or straight chain $C_1$ to $C_5$ alkoxyl group. Yet other preferred prodrugs according to the invention have formulas in which $R^1$, $R^2$, $R^4$ and $R^5$ are selected from the same branched or straight chain $C_1$ to $C_5$ alkoxyl group. One particularly cysteine prodrug according to the invention has the structure:

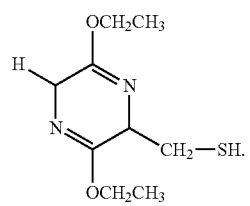

Cysteine prodrugs according to the invention are further provided in the form of cystine dimers, a particularly preferred dimer having the structure:

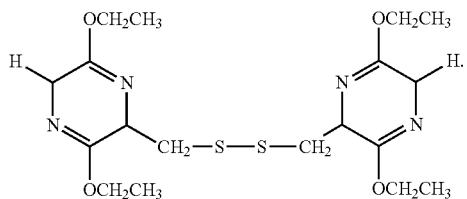

In certain embodiments, the inventive compounds will be provided as pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of the pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts, alkaline earth metal salts, e.g. calcium or magnesium salts; and salts formed with suitable organic ligands, e.g. quaternary ammonium salts. Conventional procedures for the selection and preparation of suitable prodrug derivatives are further described in, for example, Design of Prodrugs, ed. H. Bundgaard, Elsevier, 1985.

Where the compounds according to the invention have at least one asymmetric center, they may accordingly exist as enantiomers. Where the compounds according to the invention possess two or more asymmetric centers, they may additionally exist as diastereoisomers. It is to be understood that all such isomers and mixtures thereof in any proportion are encompassed within the scope of the present invention.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. It is also envisioned that the compounds of the present invention may be incorporated into transdermal patches designed to deliver the appropriate amount of the drug in a continuous fashion.

For preparing solid compositions such as tablets, the principal active ingredient is mixed with a pharmaceutically acceptable carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture for a compound of the present invention, or a pharmaceutically acceptable salt thereof. When referring to these preformulation compositions as homogeneous, it is meant that the active ingredient is dispersed evenly throughout the composition so that the composition may be easily subdivided into equally effective unit dosage forms such as tablets, pills and capsules. This solid pre-formulation composition is then subdivided into unit dosage forms of the type described above containing from 0.1 to about 500 mg of the active ingredient of the present invention. Typical unit dosage forms contain from 1 to 100 mg, for example, 1, 2, 5, 10, 25, 50 or 100 mg, of the active ingredient. The tablets or pills of the novel composition can be coated or otherwise compounded to provide a dosage affording the advantage of prolonged action. For example, the tablet or pill can comprise an inner dosage and an outer dosage component, the latter being in the form of an envelope over the former. The two components can be separated by an enteric layer which, serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium caboxymethylcellulose, methylcellulose, polyvinylpyrrolidone or gelatin.

The compounds according to the present invention exhibit schizophrenia reducing/alleviating activity, as demonstrated by standard protocols. For example, efficacy of the present inventive compounds in the schizophrenia context has been demonstrated by assaying startle response to a load stimulus (pulse) when preceded by a pre-pulse stimulus (see Examples 2-5 herein). Accordingly, another aspect of the invention provides a method for the reduction of schizophrenia in a subject in need of such treatment by administration of an effective amount of cysteine prodrug or dimer thereof. In the treatment of schizophrenia, suitable dosage level (i.e., an effective amount) is about (1-5000) mg/kg, per day, preferably about (30-3000) mg/kg per day, and especially about (50-1000) mg/kg per day. The compounds may be administered on a regimen of 1 to 4 times per day, or on a continuous basis.

As well, the compounds according to the present invention may also exhibit the ability to reduce drug cravings. This desirable activity can be shown in animal models involving drug-seeking behavior produced by stress, drug-paired cues, or a cocaine priming injection. The efficacy of compounds according to the present invention are further described in, e.g., Example 6 below. Accordingly, yet another aspect of the invention is directed to a method of reducing a drug craving in a subject in need thereof. Such a method includes the step of administering an effective amount of a compound having the chemical structure of an inventive compound described herein to the subject whereby the drug craving is reduced in the subject. In the treatment of drug cravings, suitable dosage level (i.e., effective amount) is about (1-5000) mg/kg, per day, preferably about (30-3000) mg/kg per day, and especially about (50-1000) mg/kg per day.

The following examples are, of course, offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

EXAMPLES

Example 1

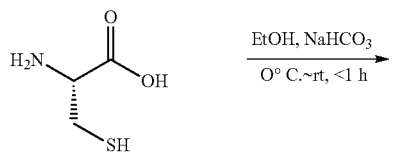

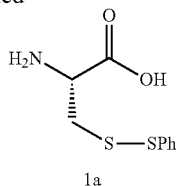

1a

C₉H₁₁NO₂S₂
Mol. Wt.: 229.32

2-Amino-3-phenyldisulfanyl-propionic acid

Preparation of Phenylsulfenyl Chloride:

Into a three-neck, round-bottom flask (1 L), fitted with an argon inlet, a pressure-equalizing dropping funnel (500 mL), and a magnetic stir bar, was charged with thiophenol (84 mL) (Note 1), dry triethylamine (1 mL), and dry pentane (400 mL) (Note 2) under a blanket of argon. The remaining neck of the flask was stoppered and the argon was allowed to sweep gently through the flask and out of the pressure-equalizing dropping funnel. The flask and its contents were cooled to 0° C. with an ice bath and stirring was begun. The dropping funnel was charged with sulfuryl chloride (76 mL) (Note 1). The sulfuryl chloride was added dropwise over a 1-hr period to the chilled thiophenol solution with stirring. During this addition, a thick layer of white solid formed. It gradually dissolved as it was broken apart. After the addition was complete, the ice bath was removed and the mixture was allowed to stir for 1 h longer while slowly warming to room temperature. During the course of the addition and subsequent stirring, the clear, pale-yellow solution became dark orange-red. The dropping funnel was replaced with an outlet adapter connected to a vacuum pump and the argon inlet was exchanged for a ground glass stopper. The pentane and excess sulfuryl chloride were removed under reduced pressure at room temperature. After this, the outlet adapter was replaced by a short-path distillation apparatus adapted for use under reduced pressure. The oily red residue was distilled to give phenylsulfenyl chloride as a blood-red liquid (26 g, 87%), by 41-42° C. (1.5 mm) (Note 3). This compound was stored under argon until used in Part B (Note 4).

Note 1. Thiophenol (97%) and sulfuryl chloride (97%) were obtained from Aldrich Chemical Company, Inc. and used without further purification.

Note 2. Both pentane and triethylamine were obtained from the Aldrich Chemical Company, Inc. Before use they were dried over sodium wire and distilled from fresh sodium wire onto Linde 4A molecular sieves under an atmosphere of argon.

Note 3. Yields of phenysulfenyl chloride of 82-92% were obtained.

L-Alanine, 3-(phenyldithio)—(1a)

To a solution of L-cysteine hydrochloride monohydrate (47 g, 0.3 mol) in absolute ethanol (900 mL) was added powdered sodium bicarbonate (30 g, 0.36 mol) at 0° C. in one portion. Phenylsulfenyl chloride (50 g, 0.345 mol) was added dropwise with stirring to the mixture. After the complete addition of the reagent, the reaction mixture was allowed to stand at room temperature and the sodium chloride which was produced during the reaction was removed by filtration. After basifying the mixture by the addition of pyridine (38 mL) into the filtrate, the fine precipitate which formed was allowed to stand for a couple of hours, then filtrated and washed well with ethanol and dried to provide the crude product as a white solid. After recrystallization from aqueous HCl (0.5 N, 4000 mL), the final product S-thiol-phenyl-L-cysteine 1a was obtained (52 g) in 76% yield as colorless plates. m.p. 192° C. (decomp). ¹H NMR (CD₃CO₂D): δ 3.53-3.76 (m, 2H), 4.89 (t, 1H), 7.26-7.88 (m, 5H); ¹³C NMR (75.5 MHz, CD₃CO₂D): δ 35.5, 52.5, 127.6, 128.5, 129.1, 129.3, 133.5, 171.6. This material was employed directly in the next step.

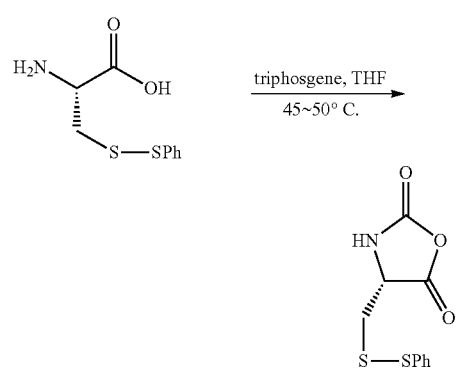

2a

C₁₀H₉NO₃S₂
Mol. Wt.: 255.32

4-Phenyldisulfanylmethyl-oxazolidine-2,5-dione 2,5-Oxazolidinedione,
4-[(phenyldithio)methyl]—(2a)

To a rapidly stirred (overhead stirrer) suspension of S-thiol-phenyl-L-cysteine 1a (57.5 g, 0.25 mol) in THF (250 mL) was added solid triphosgene (26 g, 88 mmol) in one portion at 45-50° C. (before addition, remove the heating mantle). When the temperature drops to 45° C., put the heating mantle back on and maintain the inside temperature around 45-50° C. until the solution becomes homogeneous. After the removal of the heating mantle, the solution was purged with argon overnight into a NaOH bubbler to remove any residual phosgene. The solvent was evaporated in vacuo and this provided anhydride 2a (55 g) in 85% yield: m.p. 217° C. (decomp). ¹H NMR (CDCl₃) δ 2.90-2.98 (m, 1H), 3.30 (d, 1H, J=12 Hz), 4.68 (d, 1H, J=9 Hz), 6.01 (s, 1H), 7.34-7.58 (m, 5 H); ¹³C NMR (75.5 MHz, CD₃CO₂D): δ 39.4, 56.5, 128.3, 128.9, 129.5, 135.2, 150.8, 167.7. Due to the unstable nature of this anhydride, it was stored in the refrigerator overnight under an atmosphere of argon and used immediately the next day without further purification.

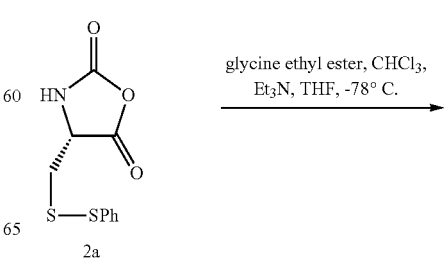

17

-continued

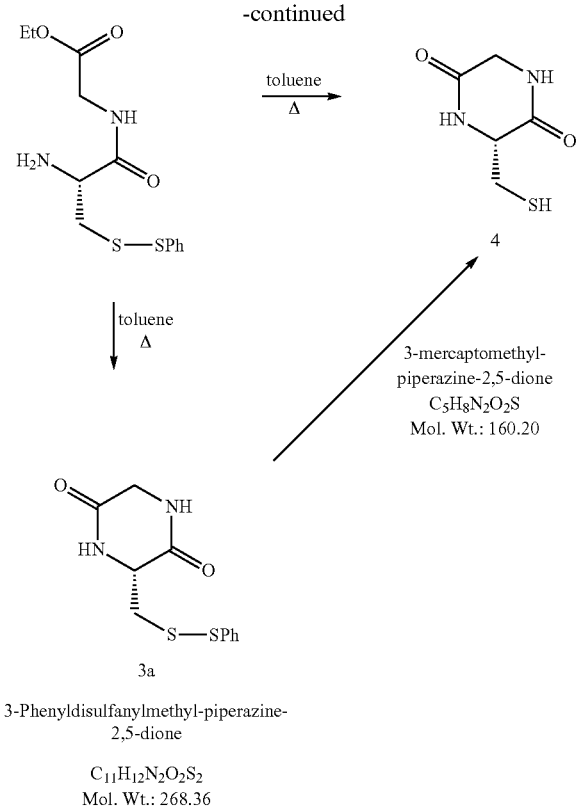

3-mercaptomethyl-piperazine-2,5-dione
C₅H₈N₂O₂S
Mol. Wt.: 160.20

3a

3-Phenyldisulfanylmethyl-piperazine-2,5-dione

C₁₁H₁₂N₂O₂S₂
Mol. Wt.: 268.36

2,5-piperazinedione, 3-(mercaptomethyl)—(4)

A solution of the N-carboxyanhydride 2a (35.7 g, 0.14 mol) in THF (160 mL) was added dropwise to a vigorously stirred (overhead stirrer) mixture of glycine ethyl ester hydrochloride (28 g, 0.16 mol), freshly distilled triethylamine (20.4 g, ~28 mL, 0.20 mol) and dry chloroform (240 mL) at −78° C. in a three-neck flask (2 L). The reaction mixture was allowed to warm to 0° C. over 8 h, and then was stirred at rt for 12 h, after which the reaction solution was filtered to remove the triethylamine hydrochloride which precipitated. The filtrate was then concentrated under reduced pressure (<40° C.) and the crude dipeptide ester was used for the preparation of the diketopiperazine 4 without further purification. ¹H NMR (CDCl₃): δ 1.29 (t, 3H), 1.93 (br, 2H), 2.74-2.82 (m, 1H), 3.40 (dd, 1H), 3.73 (dd, 1H), 4.03-4.19 (m, 2H), 4.19-4.26 (m, 2H), 7.34-7.58 (m, 5H).

b). The crude dipeptide ester (37.6 g, 0.12 mol) was heated in refluxing toluene (1000 mL) for 12 h and then cooled down to rt and kept at 0° C. for 16 h. The bislactam 4 which precipitated was isolated by vacuum filtration, washed with ether (3×150 mL), and dried under vacuum at 100° C. to provide pure diketopiperazine 4 (10.0 g) in 45% yield. The resulting filtrate produced from washing the desired diketopiperazine was evaporated under vacuum and toluene (800 mL) was added to the residue. The toluene solution was heated at reflux for another 40 h (under argon) and then the above steps were repeated to collect another 5-8 grams of diketopiperazine 4 (combined yield, 73%). 4: m.p. 258° C. ¹H NMR (DMSO-d₆): δ 3.09-3.26 (m, 2H), 3.68-3.88 (m, 2H), 4.10 (s, 1H), 8.17 (s, 1H), 8.19 (s, 1H); ¹³C NMR (500 MHz, DMSO-d₆): δ 43.5, 44.7, 54.3, 166.2, 166.6; MS (EI) m/e (relative intensity) 160(M⁺+1, 12), 140(5), 126(72), 114(100), 97(20), 85(30).

18

3-Phenyldisulfanylmethyl-piperazine-2,5-dione (3a)

c). The solution which resulted from step b above was cooled to 0° C. and keep at 0° C. for 12 h. The precipitate which resulted was filtered and provided phenyl-thiol analog 3a in 30% yield. 3a: ¹H NMR (DMSO-d₆): δ 3.09-3.21 (m, 2H), 3.65-3.82 (m, 2H), 4.10 (s, 1H), 7.11-7.55 (m, 5H), 8.18 (s, 1H), 8.20 (s, 1H); ¹³C NMR (75.5 MHz, DMSO-d₆): δ 43.5, 47.8, 54.2, 125.6, 127.7, 128.2, 129.5, 166.2, 166.6; MS (EI) m/e (relative intensity) 268 (M⁺+1, 55), 250(35), 218 (68), 159(66), 141(80), 126(70).

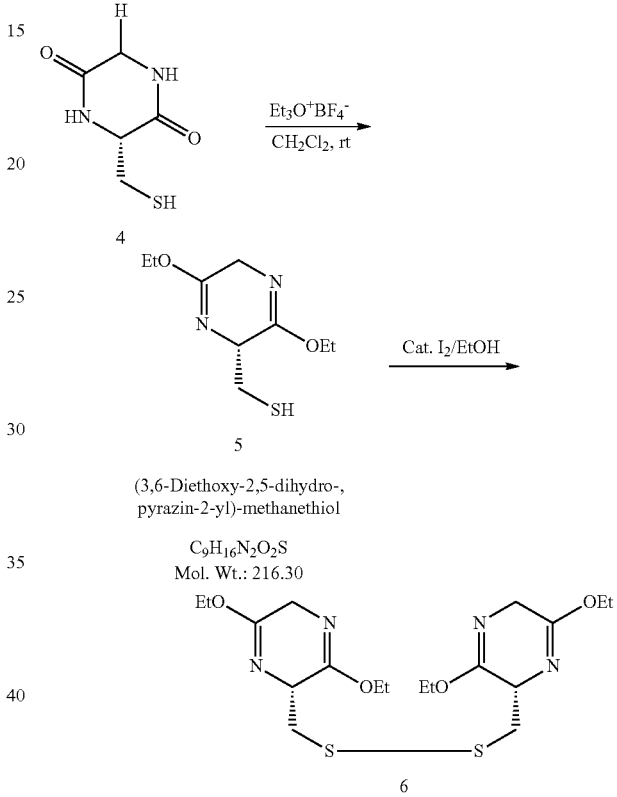

(3,6-Diethoxy-2,5-dihydro-,pyrazin-2-yl)-methanethiol

C₉H₁₆N₂O₂S
Mol. Wt.: 216.30

(3,6-Diethoxy-2,5-dihydro-pyrazin-2-yl)-methanethiol (5)

Triethyloxonium Tetrafluoroborate (Note: Triethyloxonium tetrafluoroborate is an expensive reagent; however, it is relatively easy to prepare even on large scale). A three-neck flask (500 mL), pressure equilibrating dropping funnel (125 mL) and a condenser were dried in an oven at 150° C. and assembled while hot under an atmosphere of argon. When the equipment had cooled to rt, ether [(100 mL) which had been previously dried over sodium benzophenone ketyl] and boron trifluoride diethyletherate (91 g, ~87 mL, 64 mmol) were combined [Note: On this scale the colorless BF₃ etherate was obtained from a freshly opened new bottle. If the reagent was slightly yellow or if the reaction was scaled down, the BF₃ etherate needed to be vacuum distilled first]. The ethereal solution which resulted was heated to a gentle reflux after which dry epichlorohydrin (48.8 g, ~41 mL, 51.8 mmol) was added dropwise over 1 h. The mixture was heated at reflux for an additional 1 h and allowed to stand at rt (under argon) overnight. The ether was removed by applying a positive pressure of argon in one neck of the flask while forcing the ether out through a filter stick (fritted glass tube) inserted into another neck of the flask and into a collection flask. The slightly yellow solid which remained in the flask was rinsed twice in the same manner with anhydrous ether (3×50 mL) to provide a crystalline white solid. The solid was not weighed but directly used in the next step. The following sequence was based on the yield of this reaction process at the level of 80-85%.

Dry $CH_2Cl_2$ (100 mL) was added to the flask (500 mL) which contained the freshly prepared triethyloxonium tetrafluoroborate (~42 g, 336 mmol) from the previous reaction (under argon). To this solution was added the diketopiperazine 4 (5 g, 31.2 mmol) in portions with stirring (overhead stirrer). After 2 h the reaction mixture became homogenous. The solution was stirred at rt under argon for 72 h after which the mixture was added via a cannula to an aq solution of $NH_4OH$ (14%, 100 mL) mixed with ice (100 g). The organic layer was washed with a saturated aq solution of $NaHCO_3$ (2×50 mL) and brine (80 mL) after which it was dried ($K_2CO_3$). After filtration the solvent was removed under reduced pressure to provide the bis-ethoxy lactim ether 5 as a clear yellow liquid that was further purified by flash chromatography (EtOAc:Hexane=1:4) in 71% yield (4.8 g, 22 mmol). 5: $[\alpha]_D^{26}$=+52.2° (c=2.5, $CHCl_3$). $^1$H NMR ($CDCl_3$) δ 1.32-1.36 (m, 6H), 3.27-3.30 (m, 3H), 4.08-4.22 (m, 6H), 4.39 (s, 1H); $^{13}$C NMR (75.5 MHz, $CDCl_3$): δ 14.7, 46.3, 47.5, 56.1, 61.5, 61.6, 162.7, 163.6; HRMS (ESI), cat. $(M+H)^+$: 217.2982; found: 217.2990. [Note: Previous reports employ an aq solution of $Na_2HPO_4.2H_2O$ instead of the above aq $NH_4OH$ in the workup stages of the reaction sequence. The above reaction scale (100 g of bis-lactim 5) would, however, require over 1 kg of $Na_2HPO_4.2H_2O$ and 5 L of water according to that procedure, consequently, the present procedure employing a mixture of ice and aq (14%) $NH_4OH$ (2 L total) was developed for simplicity].

Bis[(3,6-Diethoxy-2,5-dihydro-pyrazin-2-yl)-methanethiol] (6)

To the bis-ethoxy lactim ether 5 (400 mg, 1.85 mmol) in dry EtOH (10 mL) was added a catalytic amount of $I_2$ (50 mg, 10% mmol) at rt. The mixture was stirred for 6~12 h under air until analysis (TLC, silica gel) indicated the reaction was complete (new spot appeared under S.M. on the TLC plate). The organic solvent was evaporated under reduced pressure. The mixture which resulted was dissolved into EtOAc (20 mL), washed with sat. sodium thiosulfate (5~10 mL) and dried ($Na_2SO_4$). The solvent was then removed under reduced pressure which provided the dimer 6: $^1$H NMR ($CDCl_3$) δ 1.32-1.36 (m, 6H), 3.27-3.30 (m, 3H), 4.08-4.22 (m, 6H), 4.39 (s, 1H); $^{13}$C NMR (75.5 MHz, $CDCl_3$): δ 14.7, 46.3, 47.5, 56.1, 61.5, 61.6, 162.7, 163.6; The NMR spectra was identical to its monomer except the S—H bond had disappeared. HRMS (ESI) cat. $(M+H)^+$: 431.1787; found: 431.1790.

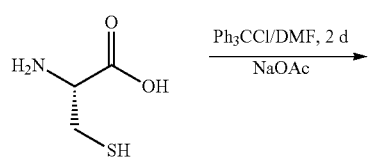

2-Amino-3-tritylsulfanyl-, propionic acid $C_{22}H_{21}NO_2S$
Mol. Wt.: 363.47

2-Amino-3-tritylsulfanyl-propionic acid (S-Trityl-L-cysteine) (1b)

L-Cysteine hydrochloride (100 g, 0.634 mol) and trityl chloride (270 g, 0.969 mol) were stirred in DMF (400 mL) for 2 days at room temperature. A 10% sodium acetate solution (3.5 L) was then added dropwise and the white precipitate which formed was filtered and washed with distilled water. Afterward, the residue was stirred in acetone at 50° C. for 30 min after which it was cooled to 0° C. and filtered. The precipitate was washed with a little acetone and diethyl ether and dried in vacuo. S-Trityl-L-cysteine 1b (205 g, 89%) was obtained as a white powder. 1b: m.p. 192° C. (decomp). $^1$H NMR (DMSO-$d_6$) δ 2.45 (dd, 1H, J=9 Hz, 12 Hz), 2.58 (dd, 1H, J=4.4 Hz, 12 Hz), 2.91 (m, 1H), 7.22-7.36 (m, 15H); $^{13}$C NMR (75.5 MHz, DMSO-$d_6$): δ 33.8, 53.7, 66.4, 127.1, 127.8, 128.1, 128.4, 129.5, 144.5, 168.4. This material was directly used in the next step without further purification.

4-tritylsulfanylmethyl-, oxazolidine-2,5-dione $C_{23}H_{19}NO_3S$
Mol. Wt.: 389.47

4-Tritylsulfanylmethyl-oxazolidine-2,5-dione (2b) was prepared following the procedure for preparation of 2a as a brown oil in 85% yield. 2b: $^1$H NMR ($CDCl_3$) δ 2.70-2.85 (m, 2H), 3.47-3.56 (m, 1H), 5.62 (s, 1H), 7.07-7.73 (m, 15H). This material was directly used in the next step without further purification.

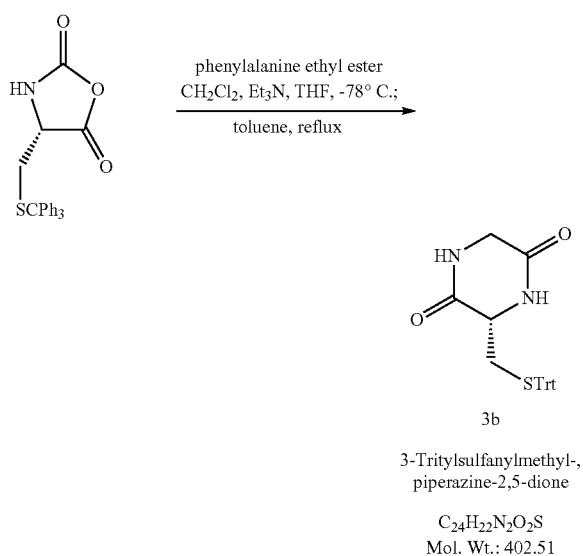

3-Tritylsulfanylmethyl-, piperazine-2,5-dione $C_{24}H_{22}N_2O_2S$
Mol. Wt.: 402.51

3-Tritylsulfanylmethyl-piperazine-2,5-dione (3b) was prepared following the procedure for preparation of 3a. 3b: m.p. 225-227° C. $[\alpha]_D^{26}$=+7.8° (c=1.05, CHCl$_3$). $^1$H NMR (CDCl$_3$) δ 2.73-2.91 (m, 2H), 3.12 (d, 1H, J=12.3 Hz), 3.95 (s, 1H), 5.80 (s, 1H), 5.82 (s, 1H), 7.20-7.62 (m, 15H). $^{13}$C NMR (75.5 MHz, CDCl$_3$): δ 35.9, 44.8, 53.0, 126.9, 128.1, 129.4, 144.0, 166.6. This material was directly used in the next step without further purification.

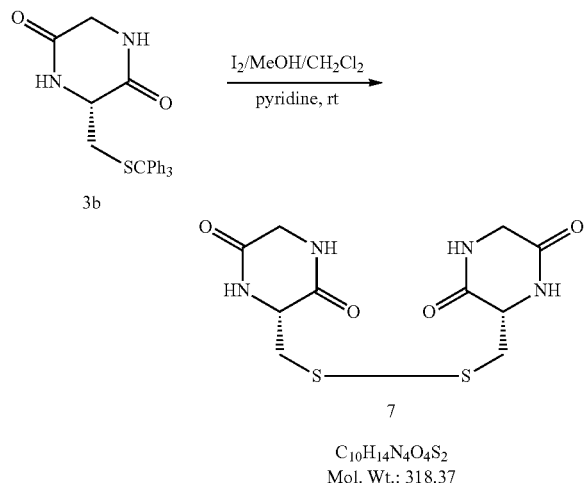

Bis[2,5-Piperazinedione, 3-(mercaptomethyl)-] (7)

The trityl protected diketopiperazine 3b (1.5 g, 3.73 mmol) was dissolved in a solution of methylene chloride (20 mL) and methanol (40 mL) with stirring. Pyridine (1.2 mL, 15 mmol) was then added to the resulting mixture, followed by a solution of iodine (0.97 g, 3.8 mmol) in methanol (5 mL). The mixture was allowed to stir for 1 h at room temperature. No precipitate had formed by this time; however, TLC analysis indicated that the reaction was proceeding slowly by the appearance of a new spot under the starting material (UV light). A precipitate began to form within 2 h after concentrating the solution to a volume of 10 mL and methanol (30 mL) was added to result in a total volume of 40 mL. The solution was stirred an additional 23 h and the precipitate was filtered off. The solid was washed with cold methanol and then decolorized by shaking with 10% aqueous sodium bisulfite (10 mL). The precipitate was filtered and dried to yield dimer 7 as white solid (680 mg, 57%). 7: m.p. >300° C. $^1$H NMR (DMSO-d$_6$) δ 3.11-3.21 (m, 2H), 3.70 (d, 1H, J=0.96 Hz), 3.73 (d, 1H, J=0.99 Hz), 4.11 (s, 1H), 8.17 (s, 1H), 8.19 (s, 1H); $^{13}$C NMR (75.5 MHz, DMSO-d$_6$): δ 44.0, 45.2, 54.8, 166.7, 167.1; HRMS (ESI) cat. (M+H)$^+$: 319.0535; found 319.0533.

Example 2

Compound 7 (Scheme 1) Produces a Larger Increase in Glutamate in the Prefrontal Cortex Relative to NAC FIG. 1 is a bar graph depicting extracellular glutamate in the prefrontal cortex (compared to baseline) following administration of cysteine prodrugs N-acetylcysteine (60 mg/kg, IP; N=4) or compound 7 (30 mg/kg, po; N=1) in rats. These results indicate a much larger peak increase in glutamate was obtained for compound 7 relative to N-acetylcysteine. Compound 7 was given to the animal orally, and thereby subjected to potential first-pass metabolism. Conversely, N-acetylcysteine was given IP in order to avoid extensive first pass metabolism that would occur following oral administration. Thus, compound 7 produced a larger relative increase in glutamate in rats as compared to NAC even though NAC was given in its preferred route of administration and at twice the concentration. This increased glutamate level indicates that compound 7 is successful in elevating extracellular cystine levels and driving cystine-glutamate exchange, a phenomenon understood to be beneficial in overcoming schizophrenia and/or drug addiction.

Example 3

Efficacy of Compound 7 (Scheme 1) as a Novel Antipsychotic Agent

Figure 2:
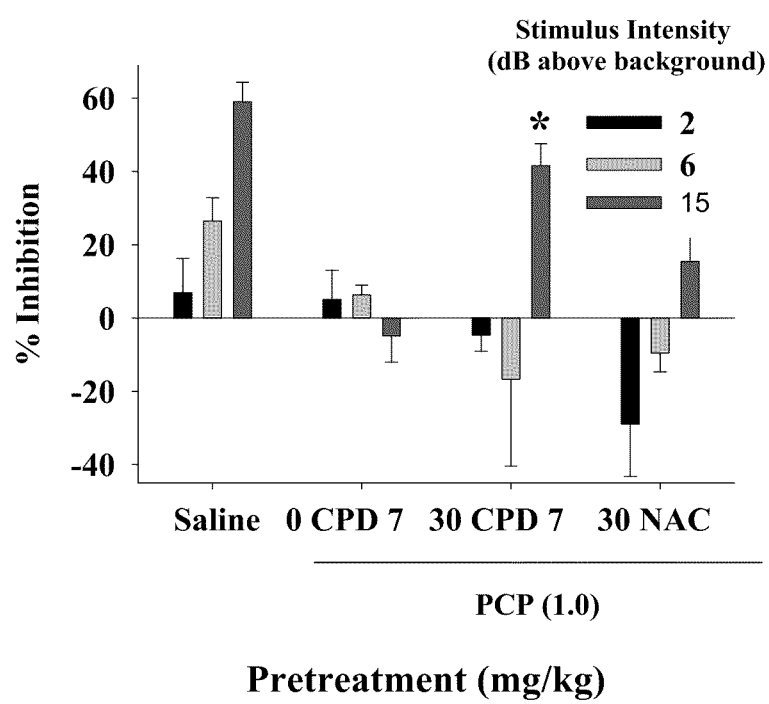
FIG. 2 provides a bar graph demonstrating inhibition of a startle response in response to a load stimulus (pulse; 110 db above background) when preceded by a pre-pulse stimulus (2-15 db above background). These data reflect sensorimotor gating because the detection of the prepulse, which signals the oncoming pulse, enables the rat to minimize the normal startle response in response to the pulse stimulus. Rats pretreated with phencyclidine only (PCP; 1 mg/kg, SC; N=5) failed to exhibit a reduction in the response elicited by the pulse even when preceded by the pre-pulse. Rats pretreated with N-acetylcysteine (30 mg/kg, po; N=5) 60 min prior to phencyclidine administration exhibited a trend toward improved sensorimotor gating (p=0.1). Rats pretreated with compound 7 (Scheme 1), (30 mg/kg, po; N=4) exhibited a significant improvement in sensorimotor gating relative to PCP controls and rats receiving NAC+PCP (Fisher LSD, p<0.05).

FIG. 2 is a bar graph illustrating inhibition of a startle response in response to a load stimulus (pulse) when preceded by a pre-pulse stimulus (2-15 db above background). Prepulse inhibition is a commonly used paradigm to screen antipsychotic agents for use in treating schizophrenia. The pre-pulse stimulus in the present study reduced the startle response in saline controls (N=5) by >60% relative to the response elicited following exposure to the pulse only. Rats pretreated with phencyclidine only (PCP; 1 mg/kg, SC; N=5) failed to exhibit a reduction in the response elicited by the pulse even when preceded by the pre-pulse. This reflects sensorimotor gating deficits common to patients afflicted with schizophrenia. Rats pretreated with N-acetylcysteine (30 mg/kg, po; N=5) 60 min prior to phencyclidine administration exhibited a trend toward improved sensorimotor gating (p=0.1). Rats pretreated with compound 7 (30 mg/kg, po; N=4) exhibited a significant improvement in sensorimotor gating relative to PCP controls and rats receiving NAC+PCP (Fisher LSD, p<0.05). Collectively, these data indicate efficacy of compound 7 as a novel antipsychotic that exceeds the potential of N-acetylcysteine.

Example 4

N-acetylcysteine & PCP-Induced Deficits in Prepulse Inhibition

Figure 3:
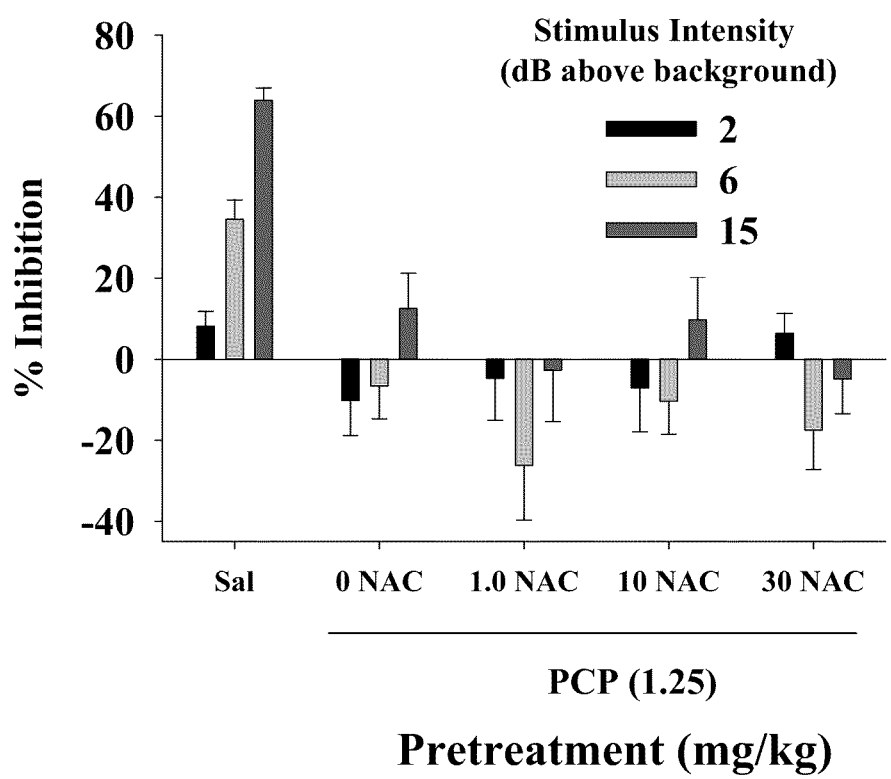
FIG. 3 depicts a bar graph illustrating the impact of N-acetylcysteine administered orally on deficits in prepulse inhibition produced by phencyclidine.

The following data set illustrate the present drawbacks associated with N-acetylcysteine, specifically the extensive hepatic metabolism and poor blood brain permeability. FIG. 3 depicts the impact of N-acetylcysteine administered orally on deficits in prepulse inhibition produced by phencyclidine. As described below, deficits in prepulse inhibition following administration of phencyclidine represent one of the most common preclinical paradigms used to screen potential antipsychotic agents. Oral administration of N-acetylcysteine (administered 60 min prior to testing; N=7-10/group), which is subjected to hepatic metabolism, fails to significantly attenuate deficits in prepulse inhibition produced by phencyclidine (0 NAC+PCP).

Figure 4:
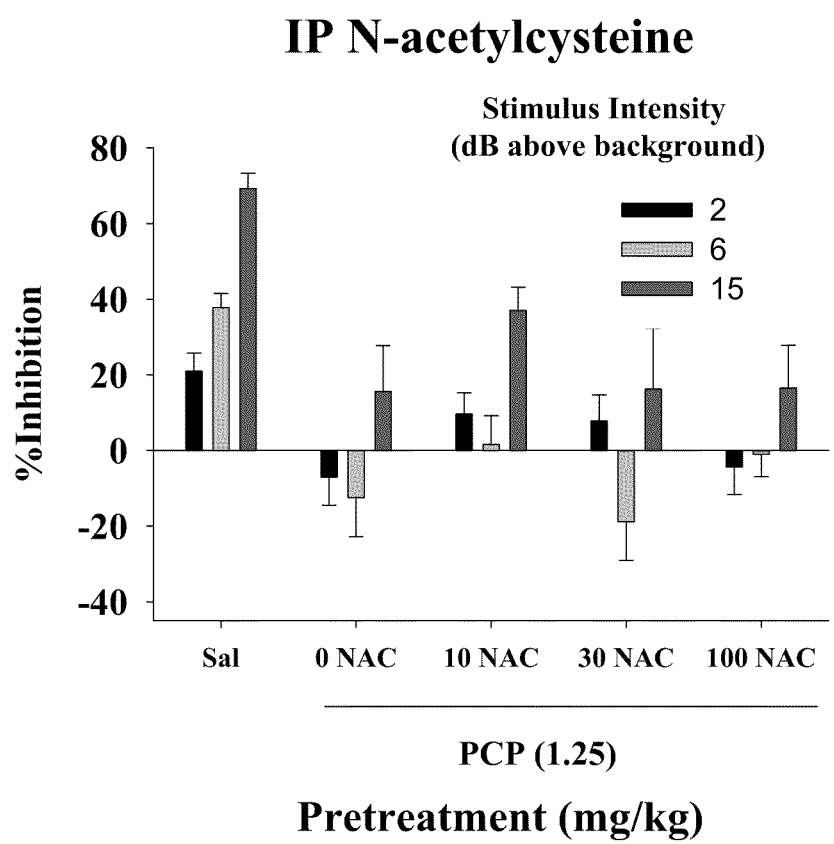
FIG. 4 shows a bar graph demonstrating the impact of N-acetylcysteine when administered into the intraperitoneal cavity of rodents in order to circumvent hepatic metabolism.

The data depicted in the FIG. 4 illustrate the impact of N-acetylcysteine (n=5-6/group; injected 60 min prior to testing) when administered into the intraperitoneal cavity in order to circumvent hepatic metabolism. N-acetylcysteine failed to significantly restore sensorimotor gating at any of the three prepulse stimulus intensities, likely a result of poor blood brain permeability.

Figure 5:
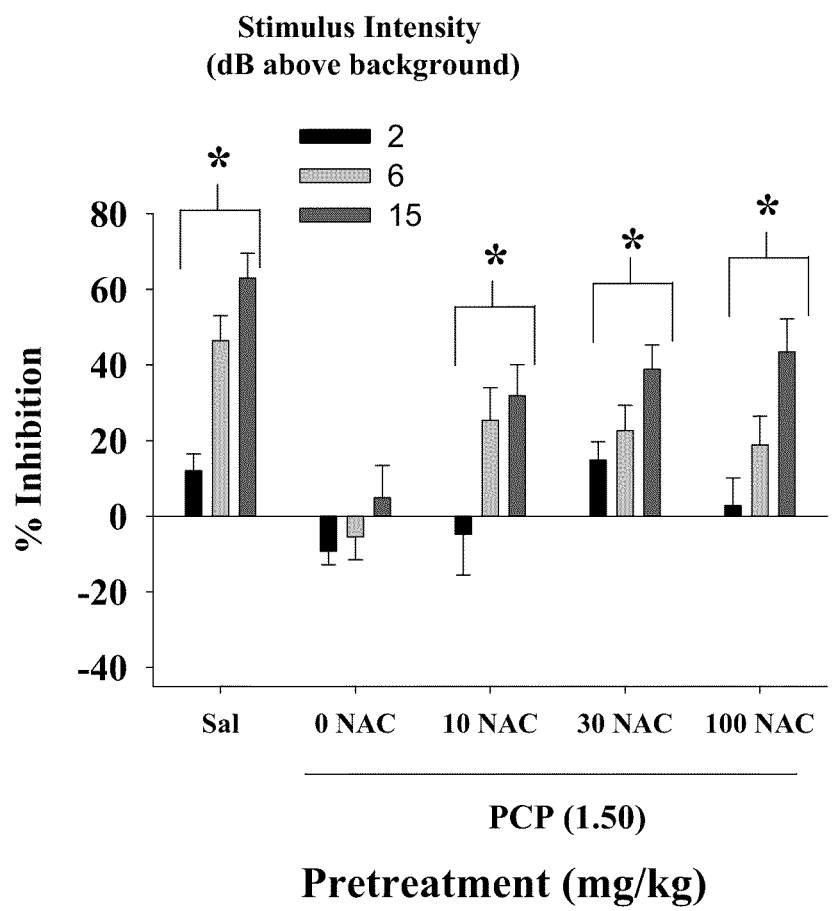
FIG. 5 provides a bar graph showing the impact of N-acetylcysteine infused directly into the rodent prefrontal cortex, the region underlying sensorimotor gating. The improved effect obtained with n-acetylcysteine when infused into the prefrontal cortex relative to oral or IP administration illustrate the problems associated with the pharmacokinetics of N-acetylcysteine.

FIG. 5 depicts the impact of N-acetylcysteine infused directly into the rodent prefrontal cortex, the region thought to underlie sensorimotor gating. Direct infusion of N-acetylcysteine (0-100 microM) circumvents the pharmacokinetic aspects of N-acetylcysteine that mitigate its use as a pharmacotherapy for schizophrenia, including extensive hepatic metabolism and poor blood brain permeability. As indicated in FIG. 5, infusion of N-acetylcysteine into the prefrontal cortex significantly restored inhibition of a startle response at each concentration tested (N=6-8/group; * indicates a significant increase relative to PCP rats receiving 0 NAC, Fisher LSD, P<0.05). Note, N-acetylcysteine-induced reversal of the effects of PCP compare favorably to the effect of clozapine, arguably the most effect antipsychotic on the market.

Example 5

Efficacy of Compounds 5 and 6 (Scheme 1) as Novel Antipsychotic Agents

Startle chambers (Kinder Scientific; 10.875"×14"×19.5") utilized for all experiments were housed in a sound attenuating chamber and mounted to a motion sensing plate. During all sessions, the background noise was held constant at 60 dB by presenting white noise through a speaker mounted above the animal. Rats underwent a 5-min habituation session prior to all matching and test sessions. Matching sessions were used to determine the magnitude of each rat's startle response to a loud auditory stimulus (pulse; 50 dB above background; 20 ms), which was assessed following the presentation of seventeen pulse stimuli (50 dB above background) presented alone and three pulse stimuli (50 dB above background) preceded by a mild auditory stimulus (prepulse; 12 dB above background; 20 ms). Rats were then assigned to treatment groups such that the magnitude of the startle response was equivalent across all groups. Test sessions consisted of 60 trials, 28 in which the pulse stimulus was presented alone (Pulse), 24 trials in which the pulse stimulus was preceded (100 ms) by a mild auditory stimulus (Prepulse; 2, 6, 15 dB above background), and 8 silent trials (No stim; background noise only). The percent prepulse inhibition was calculated as the magnitude of the startle response when the pulse was preceded by prepulse stimuli divided by the magnitude of the startle response when only the pulse stimulus is presented (×100).

Figure 6:
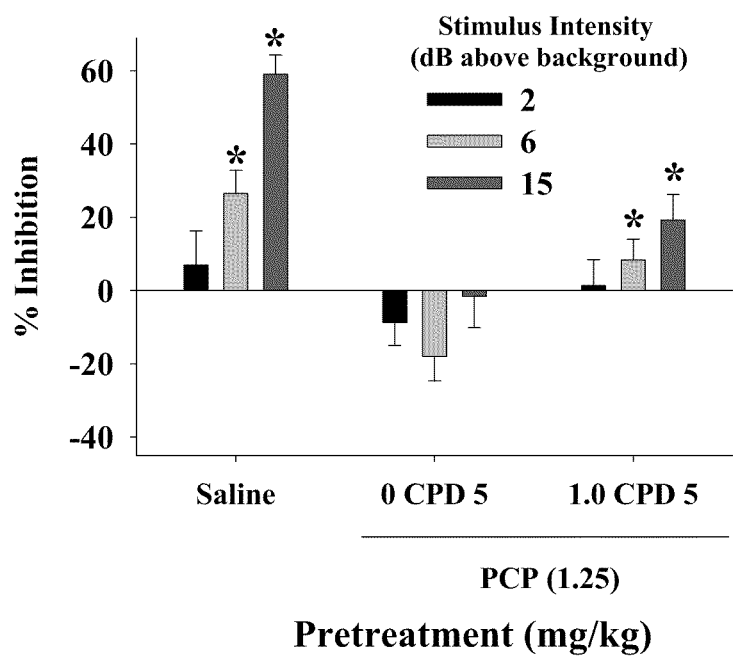
FIG. 6 depicts a bar graph illustrating the impact of compound 5 (Scheme 1) on PCP-evoked deficits in pre-pulse inhibition following oral delivery in rodents.

Prior to testing, rats received a cysteine prodrug (0-1 mg/kg, p.o.; N=9-15/group) and 50 min later an injection of PCP (0-1.25 mg/kg, SC). Ten minutes later, rats underwent the test session as described above. The novel cysteine prodrug 5, described in Scheme 1, administered orally to rodents 60 min prior to testing at a dose of 1 mg/kg produced a significant increase in sensorimotor gating as assessed by inhibition of a startle response as shown in FIG. 6 (* indicates a significant increase relative to PCP rats receiving no cysteine prodrug, Fisher LSD, P<0.05). Note, these data compare quite favorably to the results obtained with oral administration of N-acetylcysteine.

Figure 7:
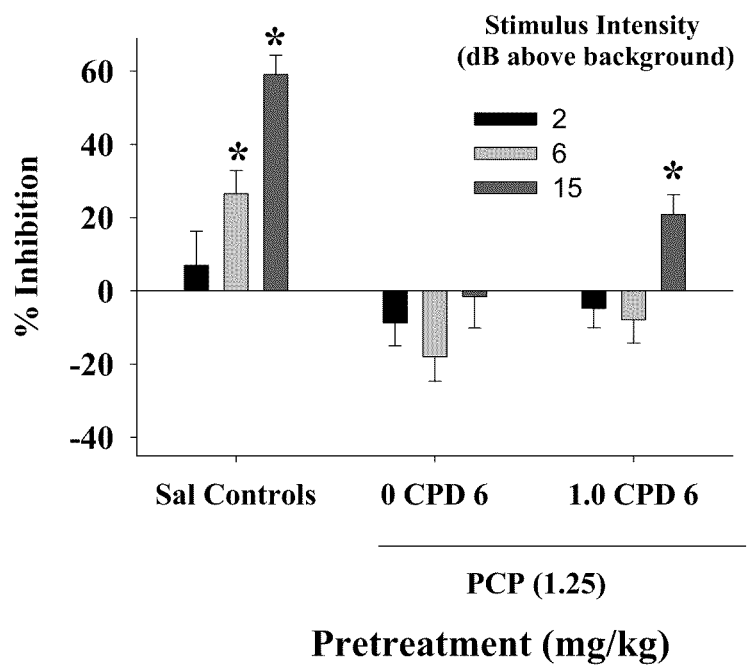
FIG. 7 depicts a bar graph illustrating the impact of compound 6 (Scheme 1) on PCP-evoked deficits in pre-pulse inhibition following oral delivery in rodents.

The data depicted in the FIG. 7 were collected as described above, except compound 6 described in Scheme 1 was administered 60 min prior to testing (N=9-11/group). As the data demonstrate, oral administration of cystine dimer 6 significantly restored sensorimotor gating at the highest prepulse intensity.

Example 6

Efficacy of Compound 5 (Scheme 1) as Novel Anticraving Agent

Figure 8:
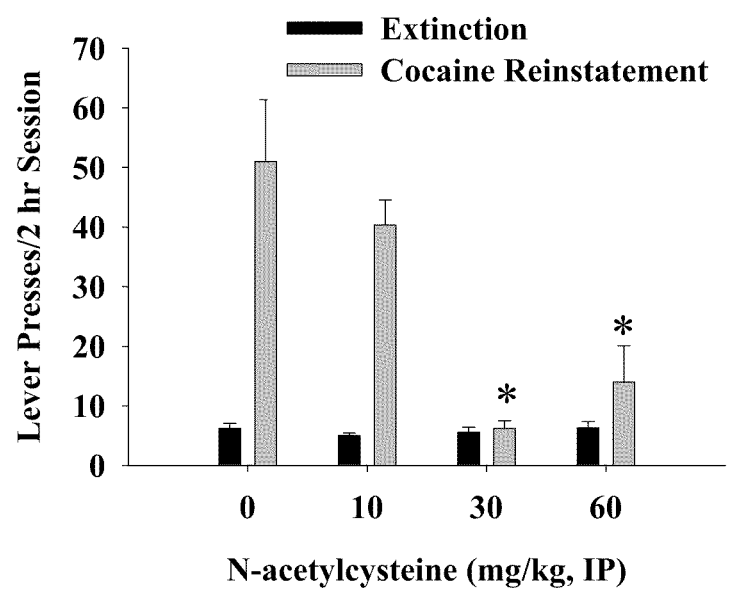
FIG. 8 provides a bar graph illustrating that N-acetylcysteine (IP) is effective in producing a significant reduction in cocaine-induced reinstatement at the doses of 30 and 60 mg/kg.
Figure 9:
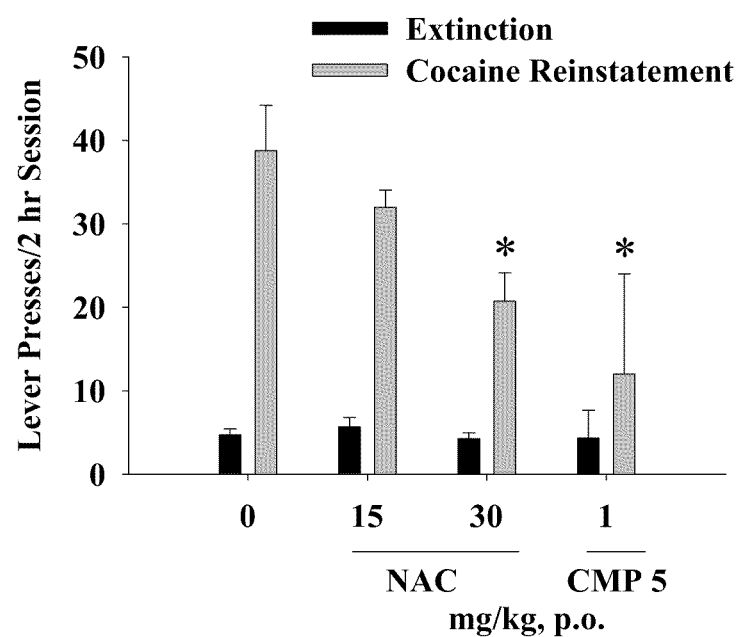
FIG. 9 depicts a bar graph illustrating that N-acetylcysteine is less effective when given orally. Further, administration of 1 mg/kg of Compound 5 (Scheme 1) was sufficient to block cocaine-induced reinstatement, an effect that was comparable to 30 mg/kg NAC.

The extinction/reinstatement paradigm represents one of the most common paradigms used to screen for potential anticraving properties of novel pharmacotherapies. In the present experiments, rats were implanted with indwelling jugular catheters with an external port affixed slightly posterior to the rat's shoulder blades. Tubing is used to connect a syringe of cocaine to the external port of the indwelling catheter. Rats are then placed into standard operant chambers (Med Associates) and permitted to press a lever for an infusion of cocaine (0.5 mg/kg/200 microL, IV). Once behavior is stable, rats are permitted at least eleven 2-hr sessions to self-administer cocaine. Afterwards, the cocaine solution is replaced with saline in order to extinguish lever pressing. Once responding decreases to 10 or fewer lever presses/2 hr sessions for 3 out of 4 daily sessions, rats are tested for reinstatement (relapse). To do this, rats are placed into the operant chamber and vehicle or a cysteine/cystine prodrug (1-60 mg/kg, p.o.; N=2-12) is administered. Afterwards, rats then receive an injection of cocaine (10 mg/kg, IP). Responding is then assessed for 120 min. Data depicted in FIG. 8 illustrate that N-acetylcysteine (IP) is effective in producing a significant reduction in cocaine-induced reinstatement at the doses of 30 and 60 mg/kg (IP; * indicates a significant decrease in responding relative to rats treated with 0 NAC, Fisher LSD). FIG. 9 demonstrates that N-acetylcysteine is less effective when given orally. Further, administration of 1 mg/kg of Compound 5 (Scheme 1) was sufficient to block cocaine-induced reinstatement, an effect that was comparable to 30 mg/kg NAC (* indicates a significant decrease in responding relative to rats treated with 0 NAC, Fisher LSD).

While this invention has been described in conjunction with the various exemplary embodiments outlined above, various alternatives, modifications, variations, improvements and/or substantial equivalents, whether known or that are or may be presently unforeseen, may become apparent to those having at least ordinary skill in the art. Accordingly, the exemplary embodiments according to this invention, as set forth above, are intended to be illustrative, not limiting. Various changes may be made without departing from the spirit and scope of the invention. Therefore, the invention is intended to embrace all known or later-developed alternatives, modifications, variations, improvements, and/or substantial equivalents of these exemplary embodiments. All technical publications, patents and published patent applications cited herein are hereby incorporated by reference in their entirety for all purposes.

What is claimed is:

1. A cysteine prodrug having the structure:

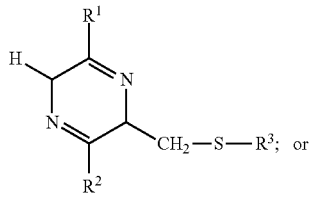

a cystine dimer of said prodrug having the structure:

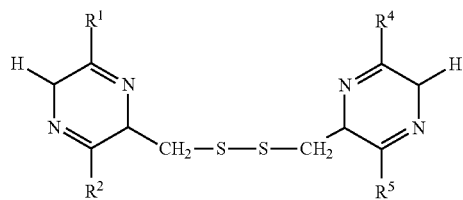

wherein: $R^1$, $R^2$, $R^4$ and $R^5$ are independently selected from OH, =O, or a branched or straight chain $C_1$ to $C_5$ alkoxy group, with the caveats that when =O is selected the nitrogen atom adjacent the carbonyl group thusly formed bears a H and a single bond joins the adjacent nitrogen to said carbonyl group and further that the $R^1$, $R^2$, $R^4$ and $R^5$ that appear in the structure shall be selected to not all be =O; and $R^3$ is H, a branched or straight chain $C_1$ to $C_5$ alkyl, a nitrobenzenesulfonyl, an aryl thio, an aryl, an alkylthio, an acyl, a benzoyl, a thio acyl, a thio benzoyl, or a benzyl group.

2. The cysteine prodrug according to claim 1, wherein said prodrug has the structure:

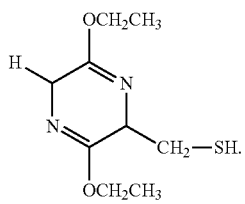

3. The cysteine prodrug according to claim 1, wherein said prodrug is the cystine dimer having the structure:

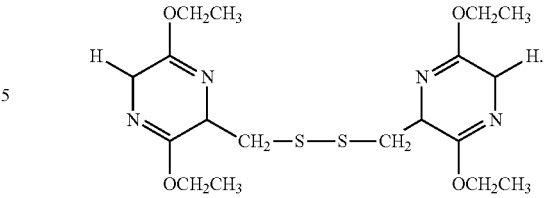

4. The cysteine prodrug according to claim 1, where said prodrug is the cysteine dimer wherein $R^1$, $R^2$, $R^4$ and $R^5$ are independently selected from a branched or straight chain $C_1$ to $C_5$ alkoxy group.

5. The cysteine prodrug according to claim 1, where said prodrug is the cysteine dimer wherein $R^1$, $R^2$, $R^4$ and $R^5$ are selected from the same branched or straight chain $C_1$ to $C_5$ alkoxy group.

6. A pharmaceutical composition comprising a cysteine prodrug or cystine dimer thereof according to claim 1 and a pharmaceutically-acceptable carrier.

7. A method of reducing drug craving in a subject comprising administering to said subject an effective amount of a prodrug or dimer thereof according to claim 1, whereby drug craving is reduced in said subject.

8. The method according to claim 7, wherein said prodrug has the structure:

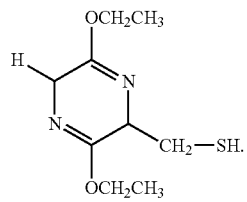 [SMILES: CCOC1=NC(CS)C(OCC)=NC1]

9. The method according to claim 7, wherein said prodrug is the cystine dimer having the structure:

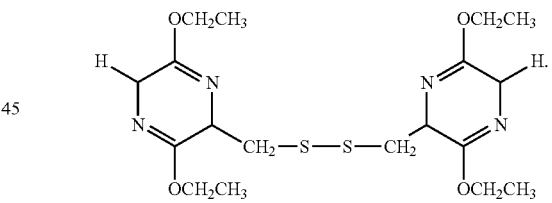

10. The method according to claim 7, wherein the step of administering to said subject is accomplished by oral delivery.

* * * * *